United States Patent

Sebag et al.

[11] 4,275,054
[45] Jun. 23, 1981

[54] DEODORANTS OR DEODORISERS AND COMPOSITIONS CONTAINING THEM

[75] Inventors: Henri Sebag; Alexandre Zysman, both of Paris; Guy Vanlerberghe, Claye Souilly, all of France

[73] Assignee: L'Oreal, Paris, France

[21] Appl. No.: 69,859

[22] Filed: Aug. 27, 1979

Related U.S. Application Data

[63] Continuation of Ser. No. 841,926, Oct. 13, 1977, abandoned.

[30] Foreign Application Priority Data

Oct. 20, 1976 [LU] Luxembourg .......................... 76035

[51] Int. Cl.³ .................... C08F 8/44; C08F 8/46; A61K 7/32; A61K 9/14
[52] U.S. Cl. .................... 424/65; 260/29.6 T; 260/112 R; 260/112.5 R; 260/325 R; 260/326.13 C; 260/326.13 R; 424/DIG. 5; 424/46; 424/47; 424/76; 424/78; 424/81; 252/305; 525/336
[58] Field of Search .................... 424/65, 47, DIG. 5, 424/76, 168; 268/326.13 C

[56] References Cited

U.S. PATENT DOCUMENTS

| | | | |
|---|---|---|---|
| 4,090,013 | 5/1978 | Ganslaw et al. | 424/65 |
| 4,156,067 | 5/1979 | Gould | 424/65 |

*Primary Examiner*—Dale R. Ore
*Attorney, Agent, or Firm*—Cushman, Darby & Cushman

[57] ABSTRACT

A polyanionic polyamide salt which comprises chain units of the formula:

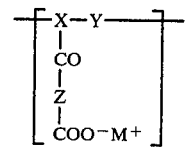

in which X denotes

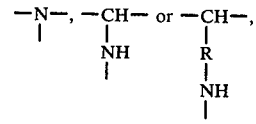

R being an aliphatic radical containing 1 to 4 carbon atoms, each Y independently denotes a divalent aliphatic or cycloaliphatic radical, Z denotes a divalent radical of the formula:

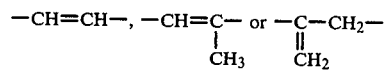

and $M^+$ denotes a sodium or potassium ion or a quaternary ammonium ion of the formula:

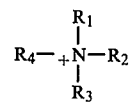

in which each of $R_1$, $R_2$, $R_3$ and $R_4$ independently denotes a hydrogen atom or a methyl, ethyl, hydroxymethyl, hydroxyethyl, hydroxypropyl, methylhydroxypropyl or methyl-dihydroxypropyl radical, the viscosity of a 5% by weight aqueous solution of the salt being from 1 to 500 centipoises at a temperature of 25° C., are provided which act as deodorants and deodorisers.

32 Claims, No Drawings

DEODORANTS OR DEODORISERS AND COMPOSITIONS CONTAINING THEM

This is a continuation of application Ser. No. 841,926 filed Oct. 13, 1977, now abandoned.

The present invention relates to unsaturated polyanionic polyamides which can be used as body deodorants or as air deodorisers, as well as to the compositions containing them.

A large number of compounds intended to slow down the secretion of perspiration or to limit its decomposition is already known. These are, in general, either antiperspirants or bactericides.

Typical antiperspirants include various basic salts of aluminium, such as the chloride and lactate.

Suitable bactericides destroy the bacterial flora which is responsible for the degradation of the perspiration. These compounds are halogenated aromatic compounds such as hexachlorophene, quaternary ammonium compounds such as benzalkonium chloride, or certain antibiotics.

In contrast to these known products, the compounds of the present invention do not exhibit a significant slowing down of the secretion of perspiration, nor a germicidal activity, and hence there is no risk of their interfering with the normal development of the cutaneous bacterial flora.

The compounds of this invention are salts of polyanionic polyamides, which can be represented by a chain of units according to the following formula:

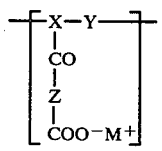
I in which X denotes

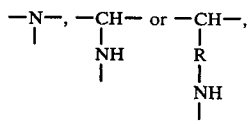

R being a divalent alkylene radical containing 1 to 4 carbon atoms, Y denotes an aliphatic or cycloaliphatic chain which can be identical or different for two successive units. Z denotes one of the following divalent radicals:

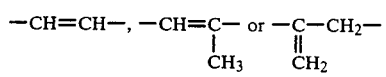

and $M^+$ denotes a sodium or potassium ion or a quaternary ammonium ion of the formula:

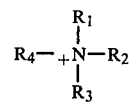

in which each of $R_1$, $R_2$, $R_3$ and $R_4$ independently denotes a hydrogen atom or a methyl, ethyl, hydroxymethyl, hydroxyethyl, hydroxypropyl, methylhydroxypropyl or methyl-dihydroxypropyl radical.

Numerous tests carried out "in vitro" on a sample of human perspiration, and "in vitro" on human beings, have shown a very marked activity of these compounds as odour absorbers.

Furthermore, we have found that the saturated derivatives corresponding to the compounds of the invention are inactive. Accordingly it is believed that the presence of the double bonds in the compounds play an important role in the elimination of body odours.

The compounds of the invention can easily be prepared by a known type of condensation process, by reacting an acid anhydride of the formula:

with a cationic polymer or oligomer having recurring units of the formula: $+XH-Y+$ (and containing primary or secondary amino groups in the main chain or in side-chains) and neutralising the acid with an organic or inorganic basic reactant of the formula: BM; in these formulae, X, Y, Z and M are as defined above and $B^-$ denotes the anion associated with $M^+$. Amongst the cationic polymers or resins which can be used having recurring units $+XH-Y+$, there may be mentioned, by way of example, natural proteins such as casein, basic polyamino-acids such as the polylysines, and synthetic polymers such as the polyethyleneimines, the polyvinylamines and the poly-aminoamides which are preferred. These include optionally cross-linked polycondensates of diacids and linear or branched polyamines, and especially the crosslinked or non-crosslinked polyaminoamides described in U.S. Ser. No. 762,804, the disclosure of which is hereby incorporated by reference, such as the polymer comprising the chain unit $+CO-(CH_2)_4-CONH-(CH_2CH_2NH)_n+$, the polymer comprising the chain unit:

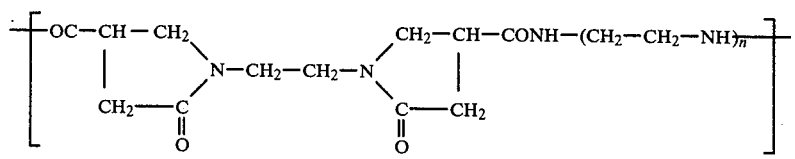

the polymer comprising the chain unit $+OC-CH_2-CH_2-NH-CH_2-CH_2-NH-CH_2-CH_2-CONH-(CH_2-CH_2-NH)_n+$, and the polymer comprising the chain unit

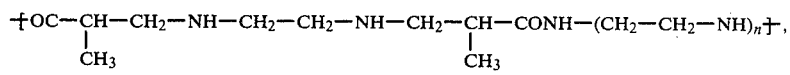

n having a value of 2 or 3, as well as polymers which can contain more than one of these units.

The polyamino-polyamide of U.S. Ser. No. 762,804 is prepared by the polycondensation of an acidic compound on a polyamine. The acidic compound is selected from the group consisting of:

(i) an organic dicarboxylic acid,
(ii) an ethylenically unsaturated aliphatic mono- or di-carboxylic acid,
(iii) an ester of said acids, preferably with a lower alkanol having from 1-6 carbon atoms, and
(iv) mixtures of these compounds.

The polyamine usefully employed to produce the polyamino-polyamide is selected from the group consisting of bis primary and mono- or bis-secondary polyalkylenepolyamines. 0–40 mole percent of the selected polyamine can be replaced by a bis-primary amine, preferably, ethylenediamine or by a bis-secondary amine, preferably piperazine and 0–20 mole percent of the selected polyamine can be replaced by hexamethylene-diamine.

Crosslinking of the polyamino-polyamide is effected with a crosslinking agent selected from the group consisting of epihalohydrins, diepoxides, dianhydrides, unsaturated anhydride and the bis unsaturated derivatives, and is characterized by the fact that the crosslinking agent is employed in amounts of 0.025–0.35 mole of crosslinking agent per amine group of the polyaminopolyamide and generally from 0.025 up to about 0.2 mole and, in particular, from 0.025 to up to about 0.1 mole of crosslinking agent per amine group of the polyamino-polyamide.

Representative specific acids usefully employed in the production of the polyamino-polyamides are selected from the group consisting of saturated aliphatic dicarboxylic acids having from 6 to 10 carbon atoms for example adipic acid, 2,2,4-trimethyl and 2,4,4-trimethyl adipic acids; aromatic dicarboxylic acids such as terephthalic acid; and ethylenically unsaturated aliphatic mono- and di-carboxylic acids such as acrylic acid, methacrylic acid and itaconic acid. Adipic acid is particularly preferred.

The esters of the above mentioned acids can also usefully be employed as can mixtures of two or more of said carboxylic acids or their esters.

Representative specific polyamines usefully employed in the preparation of the polyamino-polyamides are selected from the group consisting of the bis primary and mono- or bis-secondary polyalkylene-polyamines, such as diethylene triamine, dipropylene triamine, triethylene tetraamine and their mixtures.

The polycondensation reaction is carried out in accordance with known procedures, by mixing the initial reactants; heating the resulting mixture to a temperature between about 80°–250° C., and preferably between about 100°–180° C., for 1–8 hours. The choice of the exact reaction time and temperature can depend on the choice of the particular initial reactants selected but the same is easily determined by those skilled in the art. After heating the reaction mixture according to the above schedule, the same is then subjected to total reflux for about 0.5–1 hour so as to eliminate the water or alcohol formed during the course of the polycondensation. Reflux is initially carried out at atmospheric pressure and then at sub-atmospheric pressure. The polycondensation reaction is also generally carried out under a nitrogen atmosphere to avoid any significant colorations and to facilitate the elimination of volatile substances.

In carrying out the polycondensation reaction, the dicarboxylic acid is preferably employed in equimolar proportion relative to the primary amine groups of the polyalkylene-polyamine. According to a preferred embodiment of the present invention, the polycondensation of the polyalkylene-polyamine selected preferably from the group of diethylene triamine, triethylene tetramine, dipropylene triamine and mixtures thereof is effected with either (1) a carboxylic diacid, preferably adipic acid or dimethyl ester, or (ii) the intermediate product of addition of one molecule of ethylenediamine and two molecules of the methyl ester of an ethylenically unsaturated acid such as methyl acrylate, methyl methacrylate or methyl itaconate.

The addition reaction of ethylenediamine on the said unsaturated ester is carried out by mixing the reactants at a temperature between 5°–80° C. The polycondensation reaction is effected by heating the reactants for 30–60 minutes at reflux followed by eliminating the methyl alcohol formed, at a temperature of 120°–150° C., or of the water formed at a temperature of 140°–175° C., initially under atmospheric pressure and finally under sub-atmospheric pressure of 15 mm of mercury. The polyamino-polyamides thus obtained have a viscosity in a 10% aqueous solution at 25° C. lower than 3 centipoises.

The preferred anhydrides are maleic anhydride, itaconic anhydride and citraconic anhydride.

Suitable basic reactants include inorganic bases such as sodium hydroxide, potassium hydroxide and ammonia, organic bases such as monoethanolamine, diethanolamine, triethanolamine, triisopropanolamine, N-methylethanolamine or N-ethylethanolamine, N,N-dimethylethanolamine or N,N-diethylethanolamine, 2-methyl-2-amino-propanol, 2-methyl-2-amino-propane-1,3-diol and tris-hydroxymethylaminomethane, and alkali metal alcoholates such as sodium methylate or ethylate.

The reaction of the anhydride with the polyamine can be carried out in solvents such as isopropanol or dimethylformamide or, preferably, in water or other aqueous medium.

The anhydrides and the basic reactants are conveniently added alternately and preferably in portions.

The molar ratio of anhydride to primary or secondary amine groups of the cationic resin is generally from 1:1 to 1.5:1 and preferably from 1:1 to 1.25:1.

The basic reactants are used in a sufficient amount to neutralise the acid formed, that is to say this amount is equal to (A) − (B) if (A) denotes the number of acid equivalents corresponding to the anhydride used in accordance with the present invention and (B) denotes the number of basic equivalents of the cationic resin.

The concentration of cationic resins in the reaction solvent is generally from 5 to 40% and preferably from 10 to 30% by weight. The reaction temperature is typically from 0° to 100° C. and preferably from 10° to 30° C. The degree of conversion is usually from 85 to 100%.

The polyanionic polyamides according to the invention, can be isolated from the reaction mixture by, for example, precipitation using a non-solvent, or by evaporation.

It is also possible, for aqueous reaction mixtures, to spray the latter, optionally in the presence of a filler such as dextrin or starch, introduced in an amount up to 50% by weight relative to the solids content.

The compounds of this invention can be fractionated and/or purified by dialysis. In particular, the salts of diacids, which can be present in large amounts if an excess of anhydride is used, can be removed in this way. Before carrying out the dialysis operation, it may be necessary to add the amount of basic reactant required to neutralise the acid groups present in the reaction medium.

The pH of the solutions of the compounds of the invention is generally from 6 to 12 and preferably from 7 to 10.

These compounds form white powders or yellow-coloured resins, which are soluble in water, and their viscosity in a 5% by weight aqueous solution at a temperature of 25° C. is from 1 to 500 centipoises. They are suitably used at concentrations from 0.2 to 100% and preferably from 0.5 to 20% (by weight).

The compositions which contain one or more polyanionic polyamide compounds of this invention can be used either as body deodorant compositions or as air deodoriser compositions. They can be in the form of, for example, aqueous or aqueous-alcoholic solutions, emulsions, sticks, powders, creams, aerosols, gels or solid cakes. Amongst the alcoholic compounds which may be present in the compositions, ethyl alcohol is the most generally used, but the compositions can also contain isopropanol, propylene glycol or glycerol. Suitable propellants for the aerosols include chlorofluorinated compounds such as trichloromonofluoromethane or dichlorodifluoromethane, or carbon dioxide, nitrous oxide or butane.

The compositions of the invention can also contain non-ionic surface-active agents such as polyoxyethylenated alcohols, alkyl ethers of polyglycerol and fatty alcohols containing 12 to 20 carbon atoms, salts of fatty acids such as the sodium, potassium, magnesium or aluminium salts, and cosmetic oils or waxes such as perhydrosqualene, paraffin oils, silicone oils, isopropyl myristate or isopropyl palmitate, as well as glycerol esters such as triglycerides or glycerol ether-esters, especially those described in U.S. Patent Application Ser. Nos. 451,593, 691,088, 602,963, 602,961 and 602,962.

The compositions can furthermore contain substances such as cosmetic resins, dextrin, starch, talc, perfumes, dyestuffs, preservatives, thickeners or gelling agents, or acids or bases which can be used in cosmetics.

Where the composition of the invention is an air deodoriser, it may be in the form of an aerosol, an aqueous gel or milk or solid sheet or cake which evaporates slowly into the atmosphere, and it advantageously contains atmospheric humidifier solvents such as the glycols.

The deodoriser aerosols of this invention may contain the propellants already mentioned, preferably in the presence of an emulsifier. The deodorising sheets or cakes contain a soap, preferably in the presence of glycol derivatives.

The compositions of the present invention can also be in the form of aerosols for use in ironing linen as well as in the form of deodorants for rubbish bins and for soil.

The following Examples further illustrate the present invention. Temperatures are indicated in degrees Centigrade and the percentages, unless stated otherwise, are by weight.

PREPARATION EXAMPLES

These Examples describe the preparation of compounds of the invention from polymers, the unit +X-H—Y+ of which is indicated at the start of each Example.

EXAMPLE 1

108.4 g (1.106 mols) of maleic anhydride and 110.6 g (1.106 mols) of 40% strength sodium hydroxide solution are added, in the following manner, to 200 g (1.106 basic equivalents) of a polyamino-amide resin comprising the unit +HN (CH$_2$CH$_2$)NH(CH$_2$CH$_2$)NHCO(CH$_2$)$_4$CO+ described in the applicant company's U.S. Patent Application No. 762,804, the resin being dissolved in 1,800 g of water:

The anhydride and the sodium hydroxide are added alternately at 15° C., under a stream of nitrogen, in four equal portions. The duration of addition of one portion of anhydride is 20 minutes, and this is followed by 5 minutes' stirring. Each sodium hydroxide portion is added in 5 minutes and is followed by 5 minutes' stirring.

By adding 111 g of water, a limpid solution of green-yellow colour is obtained, having a solids content of 10%.

5.1 g of 40% strength NaOH are added to 1,000 g of the above solution and the mixture is subjected to dialysis (using a dialysis tube of lay-flat width 10 cm, sold by UNION CARBIDE) under a stream of water for 19 hours.

A solution having a solids content of 8% is thus isolated, the content of sodium dimaleate, determined by thin layer chromatography, being less than 0.1%.

The viscosity at 25° C. of a 5% strength aqueous solution is 1.7 cps.

The basicity number determined with a solution of HClO$_4$ in a 60:15 mixture of CH$_3$COOH:HCOOH is 0.36 milliequivalent/g.

EXAMPLE 2

31.3 g (0.28 mol) of itaconic anhydride and 28 g (0.28 mol) of 40% strength sodium hydroxide solution are added, in the manner described in the preceding Example, to 500 g of an aqueous solution containing 50 g (0.28 basic equivalent) of the resin used in Example 1.

After adding 2.5 g of 40% strength sodium hydroxide solution, the whole of the solution is subjected to dialysis for 16 hours in 15 liters of water.

An aqueous solution having a solids content of 7.2% is thus isolated. The viscosity of a 5% aqueous solution at 25° C. is 1.5 cps. The basicity number is 0.34 milliequivalent/g.

EXAMPLE 3

26 g (0.27 mol) of maleic anhydride and 27 g (0.27 mol) of 40% strength NaOH are added, as in Example 1, to 500 g of an aqueous solution containing 50 g (0.27 basic equivalent) of resin comprising the unit:

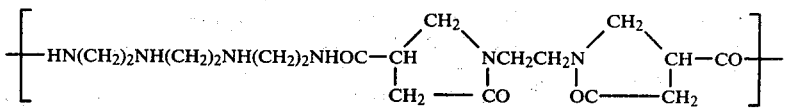

and described in the applicant company's U.S. Patent Application Ser. No. 762,804.

After adding 7.3 g of NaOH, the solution is dialysed for 20 hours in 15 liters of water. A resin solution having a solids content of 7.7% is thus isolated.

The viscosity of a 5% aqueous solution at 25° C. is 1.5 cps.

The basicity number is 0.33 milliequivalent/g.

EXAMPLE 4

70.6 g (0.72 mol) of maleic anhydride and 72 g of 40% strength NaOH (0.72 mol) are added, as in Example 1, to 1,000 g of an aqueous solution containing 100 g (0.72 basic equivalent) of a resin comprising the unit:

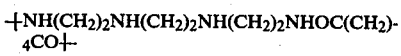

and described in the applicant company's U.S. Patent Application Ser. No. 762,804.

On adding 721 g of water, a limpid solution of resin, having a solids content of 10%, is obtained.

The basicity number is 0.42 milliequivalent/g.

EXAMPLE 5

28.4 g (0.29 mol) of maleic anhydride and 29 g (0.29 mol) of 40% strength sodium hydroxide solution are added, as in Example 1, to 1,000 g of an aqueous solution containing 100 g (0.29 basic equivalent) of a resin comprising the unit:

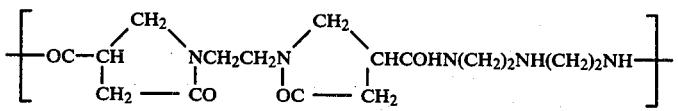

and described in the applicant company's U.S. Patent Application Ser. No. 762,804.

On adding 291 g of water, a limpid solution of resin, having a solids content of 10%, is obtained.

The basicity number is 0.26 milliequivalent/g.

EXAMPLE 6

125 g (1.275 mols) of maleic anhydride and 127.5 g (1.275 mols) of 40% strength sodium hydroxide solution are added, as in Example 1, to 2,925 g of an aqueous solution containing 292.5 g (1.275 basic equivalents) of resin used in Example 1, partially crosslinked with epichlorohydrin and having an apparent viscosity of 31 cps at 25° C., the resin being described in the applicant company's U.S. Patent Application Ser. No. 762,804.

The solution is brought to 10% solids content by adding 1.278 g of water.

After adding 2.8 g of 40% strength NaOH, 828 g of the above solution are subjected to dialysis for 18 hours in 6 liters of water.

A resin solution having a solids content of 6.4% is thus obtained.

The viscosity measured as a 5% aqueous solution at 25° C. is 21 cps.

The basicity number is 0.36 milliequivalent/g.

EXAMPLE 7

338 g (3.45 mols) of maleic anhydride and 345 g (3.45 mols) of 40% strength sodium hydroxide solution are added, as in Example 1, to 300 g of an aqueous solution of polyethyleneimine sold by Messrs. FLUKA under the name of Polymin P, and containing 2.88 basic equivalents.

After adding 119 g of 40% strength sodium hydroxide solution, 2,500 g of this solution are subjected to dialysis for 24 hours in 25 liters of water.

A resin solution having a solids content of 9.3% and a viscosity, as a 5% aqueous solution at 25° C., of 2.9 cps, is thus obtained.

The basicity number is 0.73 milliequivalent/g.

Table I below indicates the reactants used in Examples 1 to 7 as well as the characteristics of the products obtained. The columns (a) to (f) respectively indicate:
(a): the recurring unit of the starting polymer.
(b): the starting anhydride.
(c): the basic reactant used.
(d): the molar ratios (a):(b):(c).
(e): the viscosity of the final product.
(f): the basicity number of the final product.

EXAMPLE 1

Polycondensation of adipic acid and diethylenetriamine.

The structure of the polymer obtained can be characterized by repeating units of the formula $+OC-(CH_2)_4-CONH-(CH_2-CH_2-NH)_2+$ 876 g (6 moles) of adipic acid are added, with stirring and in a nitrogen atmosphere, over the course of 15 minutes, to 619 g (6 mols) of diethylene-triamine. The reaction mixture is then heated at 145°–150° C., at which temperature condensation water is noted. Refluxing is maintained for 45 minutes and then the water is removed by distillation at ambient or atmospheric pressure for 2 hours and then under reduced pressure (15 mm Hg) for 1 hour. The heating temperature increases gradually to 170° C.

The product thus obtained is cast when hot. After cooling, it is in the form of a hard, brittle and transparent yellow-green colored resin which dissolves completely in water.

EXAMPLE Ia

Crosslinking of the polymer prepared according to Example I, using epichlorohydrin.

9 g of epichlorohydrin are added, with stirring, to 200 g of resin, prepared according to the process described in Example I, dissolved in 800 g of water. The mixture is heated to 90° C. and then 1.8 g of epichlorohydrin are added in very small portions and at intervals of 5 to 10 minutes until a viscosity greater than 50 centipoises at 65° C. is obtained.

The solution is then diluted immediately until its solids content is 10%, by adding 1,098 g of water.

The apparent viscosity, measured after 24 hours and at 25° C. is 31 centipoises at a rate of shear of 26.3 seconds $^{-1}$.

The amount of crosslinking agent used is 11 mols of epichlorohydrin per 100 amine groups.

EXAMPLE Ib

Crosslinking of the polymer prepared according to Example I, using methylene bisacrylamide.

7 g of methylene bisacrylamide are added, at ambient temperature and with stirring, to 70 g of the polymer prepared according to the process described in Example I and dissolved in 280 g of water. The mixture is then heated to 80°–90° C. After heating for 1 hour, a large increase in the viscosity is observed. The mixture is then diluted until its solids content is 10% by adding 413 g of water.

A clear solution is obtained with an apparent viscosity of 32 centipoises, measured after 24 hours, at 25° C., and under a rate of shear of 26.3 seconds $^{-1}$.

The amount of crosslinking agent used is 12.1 mols of methylene bisacrylamide per 100 amine groups of the polyamino-polyamide.

EXAMPLE Ic

Crosslinking of the polymer prepared according to Example I, using N,N'-bis-epoxy-propyl-piperazine.

1.50 g of N,N'-bis-epoxy-propyl-piperazine are added, at ambient temperature and with stirring, to 20 g of polymer prepared according to the process described in Example I and dissolved in 80 g of water. The resulting mixture is then heated to 70°–80° C. After heating for 15 minutes, the mixture is diluted immediately until its solids content is 10%, by adding 113.5 g of water.

A clear solution is obtained exhibiting a viscosity of 32 centipoises measured after 24 hours, at 25° C., and under a rate of shear of 26.3 seconds $^{-1}$. The amount of crosslinking agent used is 7.3 mols of N,N'-bis-epoxy-propyl-piperazine per 100 amine groups of the polyamino-polyamide.

EXAMPLE Id

Crosslinking of the polymer prepared according to Example I, using divinyl-sulphone.

1.7 g of divinyl-sulphone are added dropwise, at ambient temperature, to 20 g of polymer prepared according to Example I and dissolved in 80 g of water, until gelling starts. The mixture is then diluted rapidly with 100 ml of water.

The apparent viscosity of the resulting 10% strength solution, measured after 24 hours, at 25° C. and at a rate of shear of 26.3 seconds $^{-1}$, is 27 centipoises.

The amount of crosslinking agent used is 13.9 mols of divinyl-sulphone per 100 amine groups of the polyamino-polyamide.

EXAMPLE II

Polycondensation of adipic acid and a mixture of diethylenetriamine and piperazine.

The structure of the polymer prepared can be represented by the two units below, distributed statistically in the proportions of 2:1.

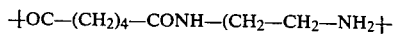

and

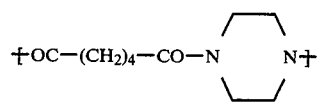

A mixture of 438 g (3 mols) of adipic acid and 86 g (1 mol) of piperazine is heated, with stirring, and in a nitrogen atmosphere, for 2 hours at 120°–135° C. 206 g (2 mols) of diethylene-triamine are then added, at this temperature and over the course of 90 minutes. The water formed is distilled for 1 hour at 140°–170° C. at atmospheric pressure, and then for 1 hour at 170°–175° C. under 15 mm Hg.

The product thus obtained is in the form of a yellow-green colored, transparent, brittle, hard resin.

EXAMPLE IIa

Crosslinking of the polymer prepared according to Example II, using epichlorohydrin.

9 g of epichlorohydrin are added, with stirring, at ambient temperature, to 200 g of resin, prepared according to Example II and dissolved in 800 g of water. The mixture is then heated to 90° C. and a further 1.1 g of epichlorohydrin are added in small portions at 5 or 10 minute intervals, until a viscosity of 50 centipoises is reached.

The solution is then diluted rapidly with 1,091 g of water in order to obtain a concentration of 10% of the crosslinked polymer.

The solution thus obtained is clear and its viscosity, measured after 24 hours, at 25° C., and at a rate of shear of 26.3 seconds $^{-1}$, is 52 centipoises.

The amount of crosslinking agent used is 13.2 mols of epichlorohydrin per 100 amine groups of the polyamino-polyamide.

EXAMPLE III

Polycondensation of adipic acid and triethylene-tetraamine.

The makeup of the polymer prepared in this example can be represented by repeating units of the formula

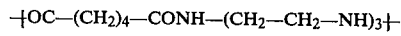

292 g (2 mols) of adipic acid are added in small portions and with stirring, under a nitrogen atmosphere, over the course of 20 minutes, to 292 g (2 mols) of triethylene-tetraamine. The mixture is then heated under full reflux at 145° C. for 1 hour. The water formed is removed by distillation at atmospheric pressure for 3 hours and under a reduced pressure of 15 mm of mercury for 1 hour, while gradually raising the temperature to 170°–175° C.

A yellow-brown colored transparent resin is thus obtained. A 10% strength solution of the polymer exhibits a viscosity, at 25° C., of less than 2 centipoises.

EXAMPLE IIIa

Crosslinking of the polymer prepared according to Example III, using epichlorohydrin.

1.8 g of epichlorohydrin are added, rapidly and with stirring, to 200 g of a 20% strength aqueous solution of polymer prepared according to the process described in Example III, and the mixture is heated at 90°–95° C. for 30 minutes. 0.4 g of epichlorohydrin is then added, at the same temperature, very slowly, until a viscosity of more than 50 centipoises, measured at 65° C., is reached.

The solution is then diluted immediately until its solids content is 10%, by adding 220 g of water. The solution obtained is clear. Its viscosity at 25° C. and at a rate of shear of 26.3 seconds $^{-1}$ is 24 centipoises. The total amount of epichlorohydrin added is 0.0242 mol, which corresponds to 7.8 mols of crosslinking agent per 100 amine groups of the polyamino-polyamide.

EXAMPLE IIIb

Crosslinking of the polymer prepared according to Example III, using methylene bisacrylamide.

0.8 g of methylene bisacrylamide is added to 100 g of a 20% strength aqueous solution of polymer prepared according to the process described in Example III. The mixture is then heated at 70°–80° C. for 25 minutes. A soft gel is then obtained which is diluted immediately until its solids content is 10%, by adding 108 g of water. The solution obtained is clear. Its viscosity, measured after 24 hours, at 25° C. and at a rate of shear of 26.3 seconds $^{-1}$, is 43 centipoises.

The amount of methylene bisacrylamide added is equivalent to 3.4 mols of crosslinking agent per 100 amine groups of the polyamino-polyamide.

EXAMPLE IV

Polycondensation of the product resulting from the reaction of 2 mols of methyl itaconate and 1 mol of ethylene-diamine with diethylene-triamine.

The structure of the polymer prepared in this example can be represented by repeating units of the formula A yellow-green colored, brittle, hard, transparent resin, which is perfectly soluble in water, is thus obtained.

EXAMPLE IVa

Crosslinking of the polymer prepared according to Example IV, using epichlorohydrin.

13 g of epichlorohydrin are added, with stirring, at ambient temperature, to 200 g of the polymer of Example IV dissolved in 800 g of water. The mixture is heated to 90° C. and a further 2 g of epichlorohydrin are added, in small portions, at 5 or 10 minute intervals, until gelling starts. The mixture is then diluted rapidly with 1,135 g of cold water in order to bring the solids content of the solution to 10%.

A clear solution is thus obtained, the viscosity of which, measured after 24 hours, at 25° C. and at a rate of shear of 26.3 seconds $^{-1}$, is 49 centipoises.

The amount of epichlorohydrin used corresponds to 22 mols per 100 amine groups of the polyamino-polyamide.

EXAMPLE IVb

Crosslinking of the polymer prepared according to Example IV, using methylene bisacrylamide.

1.5 g of methylene bisacrylamide are added, at ambient temperature and with stirring, to 50 g of polymer prepared in Example IV and dissolved in 200 g of water. The mixture is then heated to 85°–90° C. The said crosslinking agent is then added gradually until a viscosity of more than 50 centipoises at 65° C. is reached. The concentration of the mixture is then brought back to a 10% solids content, by adding 285 g of water.

A clear solution with a viscosity of 54 centipoises at $$+OC-CH-CH_2\diagdown_{N-CH_2-CH_2-N}\diagup^{CH_2-CH-CONH-(CH_2-CH_2-NH)_2+}_{C-CH_2}$$
$$\underset{CH_2-C}{\overset{|}{\underset{\parallel}{O}}}\qquad\qquad\underset{\parallel}{\overset{}{O}}$$

Step 1

118 g (1.95 mols) of ethylene-diamine are added, over the course of one hour, with stirring and under a nitrogen atmosphere, to 620 g (3.9 mols) of methyl itaconate, while maintaining the temperature at 30° C.

After the mixture has been left overnight at ambient temperature, it is heated to 80° C. in order to remove the methanol, first at atmospheric pressure and then under a reduced pressure of 15 mm Hg. The appearance of a precipitate is then noted. The reaction mixture is taken up in 500 ml of benzene and the methanol-benzene azeotrope is distilled.

The mixture is concentrated and the residue is taken up in acetone. N,N'-ethylene-bis-{2-[4'-(methylcarboxylate)] pyrrolidone}, in the form of a white powder with a melting point of 141°–142° C. and a saponification index of 6.35 milli-equivalents/gram, is thus obtained in an 82% yield.

Step 2

65.5 g (0.63 mol) of diethylene-triamine are added, at ambient temperature, to 198 g (0.63 mol) of the diester prepared in Step 1 above and the methanol formed is distilled by heating at 120°–130° C., first at atmospheric pressure for 90 minutes and then under a reduced pressure of 15 mm Hg for 30 minutes.

25° C. and at a speed gradient of 26.3 seconds $^{-1}$ is obtained.

The amount of methylene bisacrylamide added is 3.9 g and corresponds to 16 mols per 100 amine groups of the polyamino-polyamide.

EXAMPLE V

Polycondensation of a mixture of 2 mols of methyl acrylate and 1 mol of ethylene-diamine with diethylene-triamine.

The structure of the polymer prepared in this example can be represented by repeating units of the formula $$+OC-CH_2-CH_2-NH-CH_2-CH_2-NH-CH_2-CH_2-CONH-(CH_2-CH_2-NH)_2+$$

689 g (8 mols) of methyl acrylate are added, over the course of 2 hours, at a temperature of between 10° and 20° C., with stirring and under a nitrogen atmosphere, to 240 g (4 mols) of ethylene-diamine. After stirring for 1 hour at ambient temperature, 413 g (4 mols) of diethylenetriamine are added. The methanol formed is then distilled by heating at 120°–140° C. for 2 hours at atmospheric pressure and for 2 hours under a reduced pressure of 15 mm Hg.

A yellow-orange colored transparent resin is thus obtained which, in the form of a solution with a 10% solids content, has a viscosity of less than 2 centipoises.

EXAMPLE Va

Crosslinking of the polymer prepared according to Example V, using epichlorohydrin.

45 g of epichlorohydrin are added, with stirring, at ambient temperature, to 200 g of polymer prepared according to the process of Example V and dissolved in 800 g of water. The mixture is heated gradually to 90° C. and then 11 g of epichlorohydrin are added, in small portions, at 5 or 10 minute intervals, until gelling starts. The concentration is then diluted rapidly to a 10% solids content, by adding 1,500 g of cold water.

A clear solution is thus obtained with a viscosity of 25 centipoises, measured after 24 hours, at 25° C. and at a rate of shear of 26.3 seconds $^{-1}$.

EXAMPLE VI

Polycondensation of a mixture of 2 mols of methyl methacrylate and 1 mol of ethylene-diamine with diethylene-triamine.

The structure of the polymer prepared in this example can be represented by repeating units of the formula:

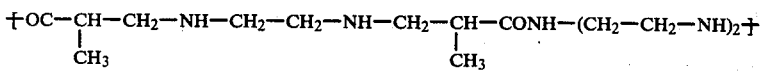

600 g of methyl methacrylate (6 mols) are added, at ambient temperature, to 180 g (3 mols) of ethylene-diamine. The mixture is left to stand for 3 days and is then heated to 80° C. for 3 hours. 309 g of diethylene-triamine (3 mols) are then added and the whole is heated at 120°–125° C. for 4 hours at atmospheric pressure and for 90 minutes under a reduced pressure of 15 mm Hg. The polycondensate thus obtained is in the form of a green-bronze colored resin.

EXAMPLE VIa

Crosslinking of the polymer prepared according to Example VI, using methylene bisacrylamide.

27.3 of methylene bisacrylamide are added, at ambient temperature and with stirring, to 84.6 g of polymer prepared according to the process described in Example VI and dissolved in 338.4 g of water. The mixture is then heated at 85°–90° C. for 15 minutes, after which it is diluted immediately until it has a solids content of 10%, by adding 669 g of water. A clear solution with a viscosity of 53 centipoises at 25° C. and a rate of shear of 26.3 seconds $^{-1}$ is obtained.

The amount of crosslinking agent added corresponds to 21.4 mols per 100 amine groups of the polyamino-polyamide.

EXAMPLE VII

Alkylation of the crosslinked polymer of Example Ia with propane sultone.

To 3000 g of a 10% aqueous solution of the crosslinked polyamino-polyamide prepared in accordance with Example Ia, having a base index of 0.45 meq/g (1 g of polymer includes $0.45 \times 10^{-3}$ amine groups), there are added, with agitation and under a nitrogen atmosphere, 113.5 g (0.93 mol) of propane sultone. The resulting mixture is then heated to 60° C. for 4 hours, after which the reaction mixture is rapidly diluted with 1020 grams of water to restore the concentration of the polymer to 10%. The solution thus obtained is yellow and exhibits at 25° C. a viscosity of 12.6 centipoises.

EXAMPLE VIII

Alkylation of the crosslinked polymer of Example Ia with sodium chloroacetate.

To 2000 g of a 10% aqueous solution of the crosslinked polyamino-polyamide prepared in accordance with Example Ia, there are added with agitation and at ambient temperature, 70 g (0.6 mol) of sodium chloroacetate. The resulting mixture is then heated to 90° C. for 10 hours after which 270 g of water are added to restore the concentration of the polymer to 10%. There is thus obtained a clear pale yellow solution having a viscosity at 25° C. of 21 centipoises.

EXAMPLE IX

Alkylation of the crosslinked polymer of Example Ia with glycidol.

To 1000 g of a 10% aqueous solution of the crosslinked polyamino-polyamide prepared in accordance with Example Ia, there are added over a two hour period with agitation and at ambient temperature, 27 g (0.36 mol) of glycidol. Agitation is continued for 5 hours and thereafter the reaction mixture is diluted with 265 g of water to restore the concentration of the polymer to 10%. There is obtained a clear, lightly colored solution having a viscosity, measured at 25° C., of 13.8 centipoises.

EXAMPLE X

Alkylation of the crosslinked polymer of Example Ia with acrylamide.

To 1000 g of a 10% aqueous solution of the crosslinked polyamino-polyamide prepared in accordance with Example Ia, there are added at ambient temperature in the presence of a trace amount of sodium nitrite, 20 g (0.28 mol) of acrylamide. The resulting reaction mixture is then heated for 10 hours at 60° C. 180 g of water are then added to the reaction mixture, thus providing a clear solution containing 10% of the polymer and exhibiting a viscosity of 11.2 centipoises at 25° C.

TABLE I

| No. | Recurring unit of the starting polymer $+HX-Y+(a)$ | (b) cyclic anhydride | (c) basic reactant | (d) ratios (a):(b):(c) | (e) viscosity in cp | (f) basicity number |
|---|---|---|---|---|---|---|
| 1 | $+HN(CH_2)_2NH(CH_2)_2NHCO(CH_2)_4-CO+$ | M A | NaOH | 1:1:1 | 1.7 | 0.36 |
| 2 | as for 1 | I A | NaOH | 1:1:1 | 1.5 | 0.34 |

TABLE I-continued

| No. | Recurring unit of the starting polymer $+HX-Y+(a)$ | (b) cyclic anhydride | (c) basic reactant | (d) ratios (a):(b):(c) | (e) viscosity in cp | (f) basicity number |
|---|---|---|---|---|---|---|
| 3 | $\left[-HN(CH_2)_2NH(CH_2)_2NH(CH_2)_2NHOC-CH\begin{smallmatrix}CH_2\\|\\CH_2-CO\end{smallmatrix}N-(CH_2)_2-N\begin{smallmatrix}CH_2\\|\\CO-CH_2\end{smallmatrix}CH-CO-\right]$ | M A | NaOH | 1:1:1 | 1.5 | 0.33 |
| 4 | $+HN(CH_2)_2NH(CH_2)_2NH(CH_2)_2NHOC(CH_2)_4-CO+$ | M A | NaOH | 1:1:1 | | 0.42 |
| 5 | $\left[-HN(CH_2)_2NH(CH_2)_2NHOC-CH\begin{smallmatrix}CH_2\\|\\CH_2-CO\end{smallmatrix}N-(CH_2)_2-N\begin{smallmatrix}CH_2\\|\\CO-CH_2\end{smallmatrix}CH-CO-\right]$ | M A | NaOH | 1:1:1 | | 0.46 |
| 6 | as for 1, crosslinked with epichlorohydrin | M A | NaOH | 1:1:1 | 21 | 0.36 |
| 7 | polyethyleneimine | M A | NaOH | 1:1.2:1.2 | 2.9 | 0.73 |

M A = maleic anhydride
I A = itaconic anhydride

EXAMPLE 8

1.86 g (0.019 mole) of maleic anhydride, 7.8 g (0.019 mole) of 10% sodium hydroxide solution are added, as described in Example 1, to 1.2 g of polyvinylamine containing 0.0196 equivalents of basic nitrogen, solubilised in 8.8 g of water. A clear solution of resin is obtained having a solids content of 16.7%, a basicity number measured in water of 0.78 milliequivalents per gram and an absolute viscosity (based on 1% active material, measured at 25° C.) of 1.13 cps.

APPLICATION EXAMPLES

The following compositions are prepared:

A. DEODORANT LOTION IN A VAPORISER

| | |
|---|---|
| Compound of Example 1 (expressed as solids content) | 2 g |
| Perfume: compound AR 5319 A from AROMESCENCE | 0.8 g |
| 96° strength alcohol | 80 ml |
| Lactic acid q.s.p. | pH 8 |
| Water q.s.p. | 100 ml |

B. AEROSOL DRY DEODORANT SPRAY

| | |
|---|---|
| Compound of Example 1 (particle size less than 40 microns) | 0.5 g |
| Micronised talc | 2 g |
| Procetyle AWS from CRODA (an alkoxylated cetyl alcohol prepared by CRODA CHEMICALS LTD) | 0.5 g |
| Isopropyl myristate | 2 g |
| Perfume concentrate PR 6045-1 from DRAGOCO | 0.2 g |
| Absolute ethyl alcohol | 3 g |
| Propellant: mixture of: trichloromonofluoromethane 60% dichlorodifluoromethane 40% | q.s.p. 100 g |

C. AQUEOUS-ALCOHOLIC AEROSOL SPRAY

| | |
|---|---|
| Compound of Example 4 | 8 g |
| Vervia C7 perfume from CREATION AROMATIQUE | 0.7 g |
| 96° strength alcohol | 80 ml |
| Water q.s.p. | 100 ml |
| $CO_2$ or $N_2O$ q.s. to give a pressure of 6 to 7 kg/cm². | |

D. EMULSION FOR PACKAGING IN A ROLL-ON BOTTLE

| | |
|---|---|
| Compound of Example 5 | 8 g |
| Oleyl/cetyl alcohol oxyethyleneated with 25 mols of ethylene oxide (per mole of alcohol) | 1 g |
| Cetyl/stearyl alcohol | 0.5 g |
| Wheat starch | 1 g |
| Dimethylpolysiloxane | 0.2 g |
| Ethyl para-hydroxybenzoate | 0.1 g |
| Propyl para-hydroxybenzoate | 0.1 g |
| Perfume consisting of Inalya No. 14,190 from FIRMENICH | 0.5 g |
| Water q.s.p. | 100 ml |

E. DEODORANT STICK

| | |
|---|---|
| Compound according to Example 1 | 5 g |
| Propylene glycol | 70 g |
| Sodium stearate | 8 g |
| Dyestuff: DC Green 5 (1% strength solution) | 0.1 g |
| Perfume (compound RDH 79-63 from ROURE BERTRAND) | 0.8 g |
| Water q.s.p. | 100 ml |

Similar deodorant or deodorising compositions are obtained by replacing the compounds respectively mentioned in compositions A, B, C, D and E by any one of the compounds of the preparation Examples 1 to 7, or by mixtures thereof, in an amount at least equal to 0.2% by weight.

F. DEODORISING SPACE AEROSOL

| | |
|---|---|
| Compound of Example 1 (30% aqueous solution) | 5.0% |
| Ethyl alcohol | 3.0% |
| Propylene glycol | 3.0% |
| Polyglycerol oleate known under the Trade name "EMCOL 14" prepared by Witco | 0.6% |
| Water | 47.4% |
| Perfume | 2.0% |
| Butane-propane 3.2 kg/cm² | 40.0% |
| | 100.0% |

G. AEROSOL PRODUCT FOR USE IN IRONING LINEN

| | |
|---|---|
| Compound of Example 1 (30% aqueous solution) | 4.0% |
| Partially hydrolysed starch | 5.0% |
| Sodium para-hydroxybenzoate | 0.2% |
| EMCOL 14 | 0.4% |
| 10% silicone emulsion | 2.0% |
| Water | 68.4% |
| Butane-propane 3.2 kg/cm² | 20.0% |
| | 100.0% |

H. SPRAY DEODORANT FOR LINEN

| | |
|---|---|
| Triethylene glycol | 3.0% |
| Ethyl alcohol | 5.0% |
| Compound of Example 1 (30% aqueous solution) | 4.0% |
| EMCOL 14 | 0.6% |
| Perfume (lavender) | 0.1% |
| Water | 67.3% |
| Butane-propane 3.2 kg/cm² | 20.0% |
| | 100.0% |

I. DEODORISING SPRAY FOR RUBBISH BINS

| | |
|---|---|
| Compound of Example 1 (30% aqueous solution) | 8.0% |
| Ethyl alcohol (denatured) | 45.9% |
| Dipropylene glycol | 3.0% |
| Quaternary ammonium compound known under the Tradename "BTC 2125" prepared by ORGANON | 3.0% |
| Perfume (pine essence) | 0.1% |
| Butane-propane 3.2 kg/cm² | 40.0% |

| -continued | |
|---|---|
| | 100.0% |
| J. DEODORISING MILK DISINFECTANT FOR SOIL | |
| Compound of Example 1 (30% aqueous solution) | 15% |
| "BTC 2125" | 1% |
| Perfume (pine essence) | 0.5% |
| Mineral oil | 2.5% |
| Cetyl alcohol polyoxyethylenated with 10 moles of ethylene oxide | 1.5% |
| Water | 79.5% |
| | 100.0% |

We claim:

1. A polyanionic polyamide salt which comprises chain units of the formula:

$$\left[\begin{array}{c} X-Y \\ | \\ CO \\ | \\ Z \\ | \\ COO^-M^+ \end{array}\right]$$

in which X denotes

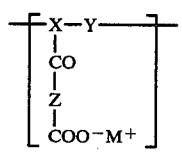

R being an aliphatic radical containing 1 to 4 carbon atoms, each Y independently denotes a divalent aliphatic or cycloaliphatic radical, Z denotes a divalent radical of the formula:

$$-CH=CH-, \quad -CH=C- \text{ or } -C-CH_2-$$
$$\phantom{-CH=CH-, \quad -CH=}\overset{|}{CH_3} \quad \overset{\|}{CH_2}$$

and M+ denotes a sodium ion, potassium ion or a quaternary ammonium ion of the formula:

$$R_4\overset{R_1}{\underset{R_3}{\overset{|}{-}\overset{+}{N}-}}R_2$$

in which each of $R_1$, $R_2$, $R_3$ and $R_4$ independently denotes a hydrogen methyl, ethyl, hydroxymethyl, hydroxyethyl, hydroxypropyl, methylhydroxypropyl or methyl-dihydroxypropyl radical, the viscosity of a 5% by weight aqueous solution of the salt being from 1 to 500 centipoises at a temperature of 25° C.

2. A salt according to claim 1 in which X and Y are such that —XH—Y— denotes the recurring units in casein, a basic polyamino acid, a polyethyleneimine, a polyvinylamine or a polyaminoamide.

3. A salt according to claim 2 in which —XH—Y— denotes —CO—(CH$_2$)$_4$—CONH—(CH$_2$CH$_2$NH)$_n$ in which n is 2 or 3.

4. A salt according to claim 2 in which —XH—Y— denotes

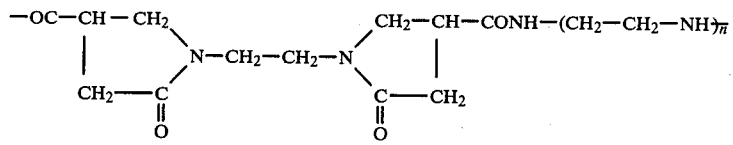

in which n is 2 or 3.

5. A salt according to claim 2 in which —XH—Y— denotes —OC—CH$_2$—CH$_2$—NH—CH$_2$—$_2$—N-H—CH$_2$—CH$_2$—CONH—$($CH$_2$—CH$_2$—NH$)_{\overline{n}}$ in which n is 2 or 3.

6. A salt according to claim 2 in which —XH—Y— denotes

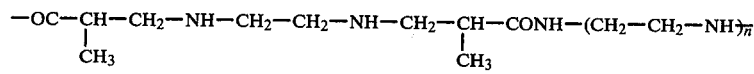

in which n is 2 or 3.

7. Process for the preparation of a salt as defined in claim 1 which comprises: (a) reacting an anhydride of an unsaturated diacid having the formula:

with a cationic oligomer or cationic polymer containing primary or secondary amine groups in the main chain or side chain comprising the recurring units of the formula:

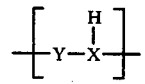

in a solvent medium selected from an aqueous medium and an inert organic solvent at a temperature ranging from 0° to 100° C. wherein the molar ratio of anhydride to said amine groups of said cationic oligomer or cationic polymer ranges from 1:1 to 1.5:1, and (b) neutralizing the acid formed with an organic or inorganic basic reactant of the formula: MB, X, Y, Z and M being defined in claim 1 and B denoting an anion.

8. Process according to claim 7 in which the solvent is isopropanol or dimethylformamide.

9. Process according to claim 7 in which the reaction is carried out at a temperature of 0° to 100° C.

10. Process according to claim 7 in which the molar ratio of anhydride to polymer is from 1:1 to 1.5:1.

11. Process according to claim 7 in which the polymer is a polyaminoamide.

12. Process according to claim 7 in which the desired product from step (b) is isolated and purified.

13. Process according to claim 12 in which the product is isolated by the addition of a non-solvent.

14. Process according to claim 12 in which the product is purified by dialysis.

15. A deodorant or deodorizing composition which contains a salt as defined in claim 1 in an amount of at least 0.2% by weight and a vehicle therefor.

16. A deodorant cosmetic composition which contains from 0.5 to 20% by weight of a polyanionic polyamide salt in a cosmetically acceptable vehicle, wherein the polyanionic polyamide salt comprises chain units of the formula:

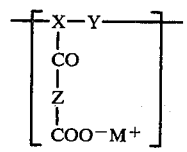

wherein X denotes

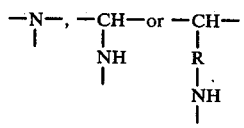

R being an aliphatic radical containing 1 to 4 carbon atoms, each Y independently denotes a divalent aliphatic or cycloaliphatic radical, Z denotes a divalent radical of the formula:

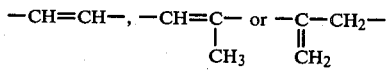

and M+ denotes a sodium ion, potassium ion or a quaternary ammonium ion of the formula:

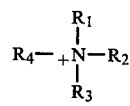

wherein each of $R_1$, $R_2$, $R_3$ and $R_4$ independently denotes hydrogen, methyl, ethyl, hydroxymethyl, hydroxyethyl, hydroxypropyl, methylhydroxypropyl or methyl-dihydroxypropyl radical, the viscosity of a 5% by weight aqueous solution of the salt being from 1 to 500 centipoises at a temperature of 25° C.

17. A deodorant cosmetic composition comprising 0.5 to 20% by weight of a polyanionic polyamide salt in a cosmetically acceptable vehicle wherein said composition is in the form of an aqueous-alcoholic lotion or oleo-alcoholic lotion, an emulsion, a stick, a powder or an aerosol, and wherein said polyanionic polyamide salt comprises chain units of the formula

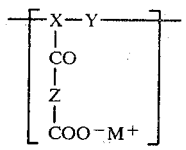

wherein X denotes

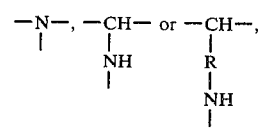

R being an aliphatic radical containing 1 to 4 carbon atoms, each Y independently denotes a divalent aliphatic or cycloaliphatic radical, Z denotes a divalent radical of the formula:

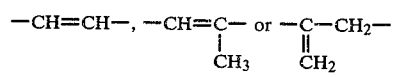

and M+ denotes a sodium ion, potassium ion or a quaternary ammonium ion of the formula

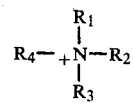

in which each of $R_1$, $R_2$, $R_3$ and $R_4$ independently denotes hydrogen, methyl, ethyl, hydroxymethyl, hydroxyethyl, hydroxypropyl, methyl-hydroxypropyl or methyl-dihydroxypropyl radical, the viscosity of a 5% by weight aqueous solution of the salt being from 1 to 500 centipoises at a temperature of 25° C.

18. A deodorising composition in the form of an aerosol, an aqueous gel or milk, solid sheet or cake, wherein said composition contains at least 0.2% by weight of a polyanionic polyamide salt and a vehicle therefor, and wherein said polyanionic polyamide salt comprises chain units of the formula

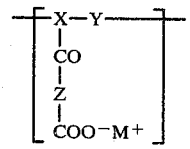

in which X denotes

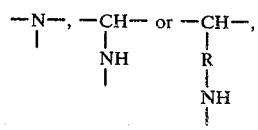

R being an aliphatic radical containing 1 to 4 carbon atoms, each Y independently denotes a divalent aliphatic or cycloaliphatic radical, Z denotes a divalent radical of the formula:

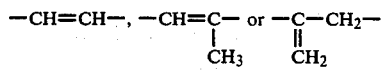

and M+ denotes a sodium ion, potassium ion or a quaternary ammonium ion of the formula:

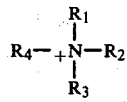

in which each of R₁, R₂, R₃ and R₄ independently denotes hydrogen, methyl, ethyl, hydroxymethyl, hydroxyethyl, hydroxypropyl, methylhydroxypropyl or methyl-dihydroxypropyl radical, the viscosity of a 5% by weight aqueous solution of the salt being from 1 to 500 centipoises at a temperature of 25° C.

19. A polymeric salt obtained by reating a polyaminoamide with an anhydride selected from maleic anhydride, itaconic anhydride and citraconic anhydride at a temperature ranging from 0° to 100° C. and neutralising the resulting acid with a sodium, potassium or quaternary ammonium base, wherein the molar ratio of anhydride to amine groups in said polyaminopolyamide ranges from 1:1 to 1.5:1.

20. A deodorant composition which contains from 0.5 to 20% by weight of a polyanionic polyamide salt in a vehicle therefor, wherein the polyanionic polyamide salt comprises chain units of the formula:

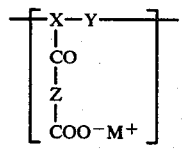

wherein X represents

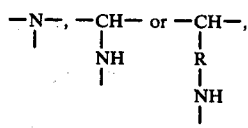

R being an aliphatic radical containing 1-4 carbon atoms, each Y independently denotes a divalent aliphatic or cycloaliphatic radical, Z denotes a divalent radical of the formula:

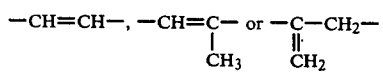

and M+ denotes a sodium ion, potassium ion or a quaternary ammonium ion of the formula:

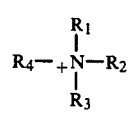

wherein each of R₁, R₂, R₃ and R₄ independently denotes hydrogen, methyl, ethyl, hydroxymethyl, hydroxyethyl, hydroxypropyl, methyl-hydroxypropyl or methyl-dihydroxypropyl radical, the viscosity of a 5% by weight aqueous solution of the salt being from 1 to 500 centipoises at a temperature of 25° C.

21. A deodorant composition comprising 0.5 to 20% by weight of a polyanionic polyamide salt in a vehicle therefor wherein said composition is in the form of an aqueous-alcoholic lotion, a cream, a gel, an emulsion, a stick, a powder or an aerosol, and wherein said polyanionic polyamide salt comprises chain units of the formula

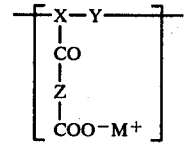

wherein X represents

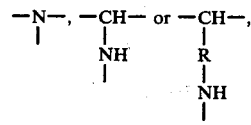

R being an aliphatic radical containing 1 to 4 carbon atoms, each Y independently denotes a divalent aliphatic or cycloaliphatic radical, Z denotes a divalent radical of the formula:

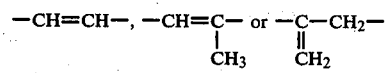

and M+ denotes a sodium ion, potassium ion or a quaternary ammonium ion of the formula

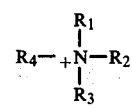

in which each of R₁, R₂, R₃ and R₄ independently denotes hydrogen, methyl, ethyl, hydroxymethyl, hydroxypropyl, methylhydroxypropyl or methyl-dihydroxypropyl radical, the viscosity of a 5% by weight aqueous solution of the salt being from 1 to 500 centipoises at a temperature of 25° C.

22. A deodorant or deodorising composition which contains a salt defined in claim 1 in an amount of at least 0.2% by weight and a cosmetically acceptable vehicle.

23. A deodorising composition in the form of an aerosol, an aqueous gel, solid sheet or cake, wherein said composition contains at least 0.2% by weight of a polyanionic polyamide salt and a cosmetically acceptable vehicle, and wherein said polyanionic polyamide salt comprises chain units of the formula:

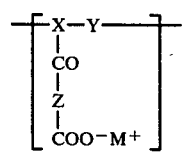

wherein X represents

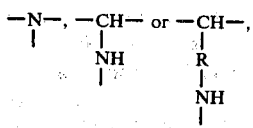

R being an aliphatic radical containing 1 to 4 carbon atoms, each Y independently denotes a divalent aliphatic or cycloaliphatic radical, Z denotes a divalent radical of the formula:

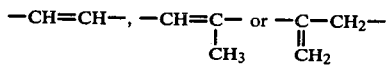

and M+ denotes a sodium ion, potassium ion or a quaternary ammonium ion of the formula:

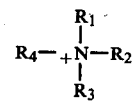

wherein each of $R_1$, $R_2$, $R_3$ and $R_4$ independently denotes hydrogen, methyl, ethyl, hydroxymethyl, hydroxyethyl, hydroxypropyl, methyl-hydroxypropyl or methyl-dihydroxypropyl radical, the viscosity of a 5% weight aqueous solution of the salt being from 1 to 500 centipoises at a temperature of 25° C.

24. A deodorant composition in aerosol or milk form which contains from 0.5 to 20% by weight of a polyanionic polyamide salt in a vehicle therefor, said vehicle comprising an effective amount of an aerosol propellant, wherein the polyanionic polyamide salt comprises chain units of the formula:

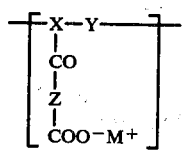

wherein X represents

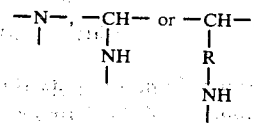

R being an aliphatic radical containing 1–4 carbon atoms, each Y independently denotes a divalent aliphatic or cycloaliphatic radical, Z denotes a divalent radical of the formula:

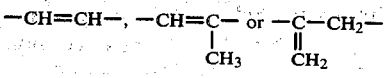

and
M+ denotes a sodium ion, potassium ion or a quaternary ammonium ion of the formula:

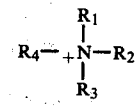

wherein each of $R_1$, $R_2$, $R_3$ and $R_4$ independently denotes hydrogen, methyl, ethyl, hydroxymethyl, hydroxyethyl, hydroxypropyl, methylhydroxypropyl or methyl-dihydroxypropyl radical, the viscosity of a 5% by weight aqueous solution of the salt being from 1 to 500 centipoises at a temperature of 25° C.

25. A method of deodorizing air using the composition of claim 24.

26. A method of ironing linen using the composition of claim 24.

27. A method of deodorizing a rubbish bin using the composition of claim 24.

28. A method of deodorizing soil using the composition of claim 24.

29. A method of deodorizing air using the composition of claim 21.

30. A method of ironing linen using the composition of claim 21.

31. A method of deodorizing a rubbish bin using the composition of claim 21.

32. A method of deodorizing soil using the composition of claim 21.

* * * * *